United States Patent [19]
Cohen et al.

[11] Patent Number: 5,549,547
[45] Date of Patent: Aug. 27, 1996

[54] FLEXIBLE TUBE HAVING A TAPERED DIAMETER PORTION FOR USE WITH ENDOSCOPIC IRRIGATION INSTRUMENTS

[75] Inventors: Herbert Cohen, Fort Lauderdale; Matthew S. Solar, Cooper City; Charles R. Slater, Fort Lauderdale, all of Fla.

[73] Assignee: Symbiosis Corporation, Miami, Fla.

[21] Appl. No.: 248,523

[22] Filed: May 24, 1994

Related U.S. Application Data

[63] Continuation-in-part of Ser. No. 959,280, Oct. 9, 1992, Pat. No. 5,314,406.

[51] Int. Cl.$^6$ ..................................................... A61M 1/00
[52] U.S. Cl. ................................................................ 604/30
[58] Field of Search ............................... 604/30, 280, 19, 604/21, 27, 28, 31, 32–34, 35, 43, 48, 51, 53, 54, 246, 247, 248, 249, 86

[56] References Cited

U.S. PATENT DOCUMENTS

| | | |
|---|---|---|
| 2,449,497 | 9/1948 | McLeod . |
| 3,208,145 | 9/1965 | Turner . |
| 3,830,225 | 8/1974 | Schinnick ................. 128/2 B |
| 3,989,033 | 11/1976 | Halpern et al. ........................ 128/2 B |
| 4,487,600 | 12/1984 | Brownlie et al. ......................... 604/35 |
| 4,519,385 | 5/1985 | Atkinson et al. ......................... 128/66 |
| 4,776,840 | 10/1988 | Freitas et al. ............................ 604/33 |
| 5,178,607 | 1/1993 | Lynn et al. ............................... 604/86 |

*Primary Examiner*—Manuel Mendez
*Attorney, Agent, or Firm*—David P. Gordon

[57] ABSTRACT

An endoscopic irrigation instrument includes a fluid chamber, a cannula coupled to a distal end of the fluid chamber, a tapered irrigation tube which couples at its proximal end to a fluid source and which couples at its distal end to an irrigation port of the fluid chamber, and a pinch valve which controls the flow of fluid from the irrigation source to the fluid chamber and hence through the cannula to the surgical site. The tapered irrigation tube is arranged so that it has a first relatively larger constant inner diameter and relatively larger wall thickness on its proximal end until it tapers down in both inner diameter and wall thickness at a location slightly proximal the pinch valve. By the time the tapered irrigation tube passes the pinch valve in the endoscopic instrument, the tapered irrigation tube is at a second relatively smaller constant inner diameter and a relatively smaller wall thickness. The tapered irrigation tube thus enables greater fluid flow, pinch valve control at the thin distal end, and tube reliability at both high and low fluid pressures.

12 Claims, 4 Drawing Sheets

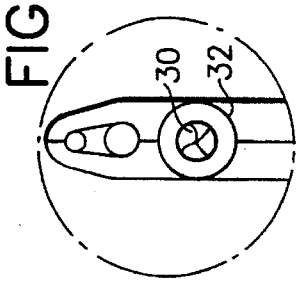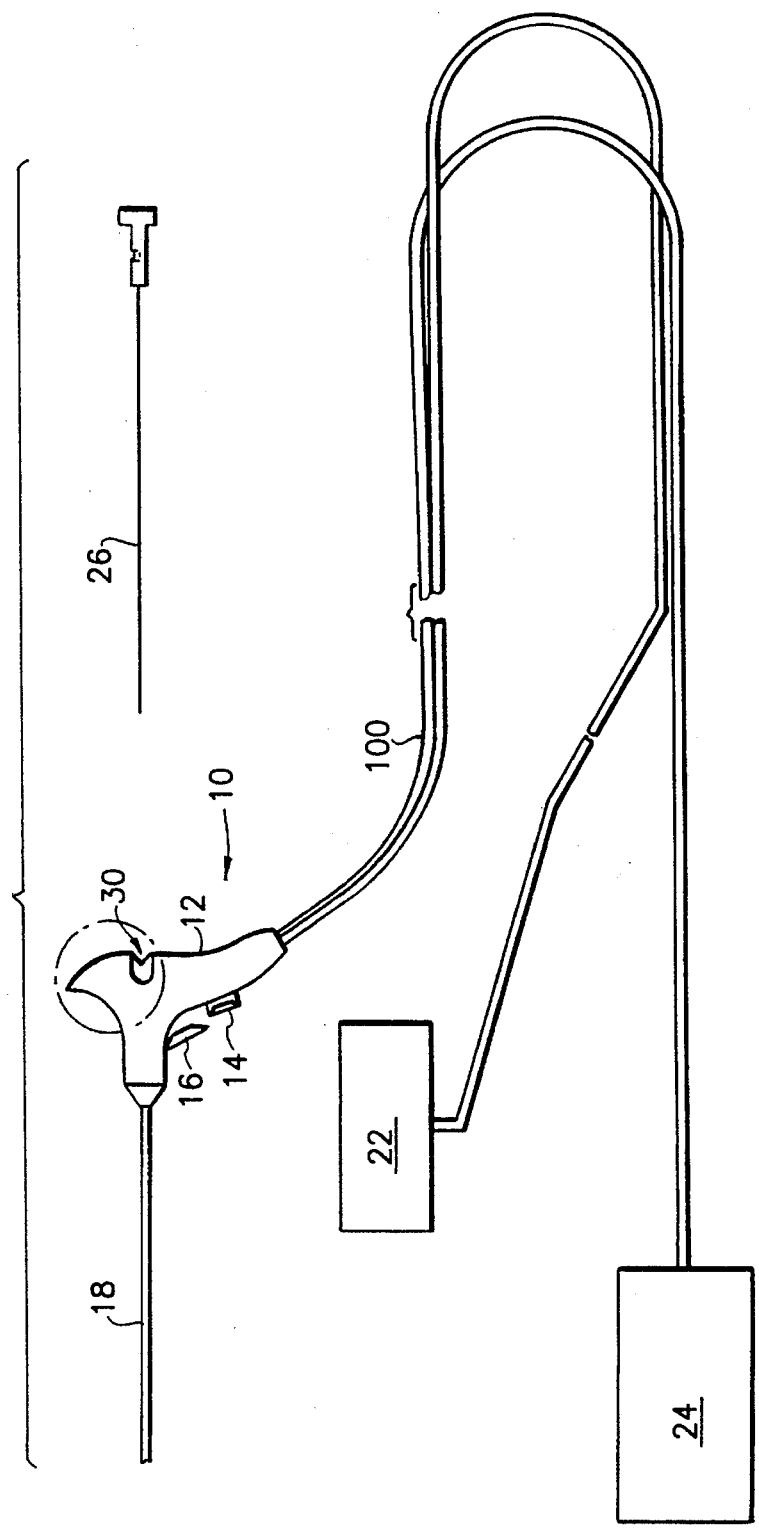

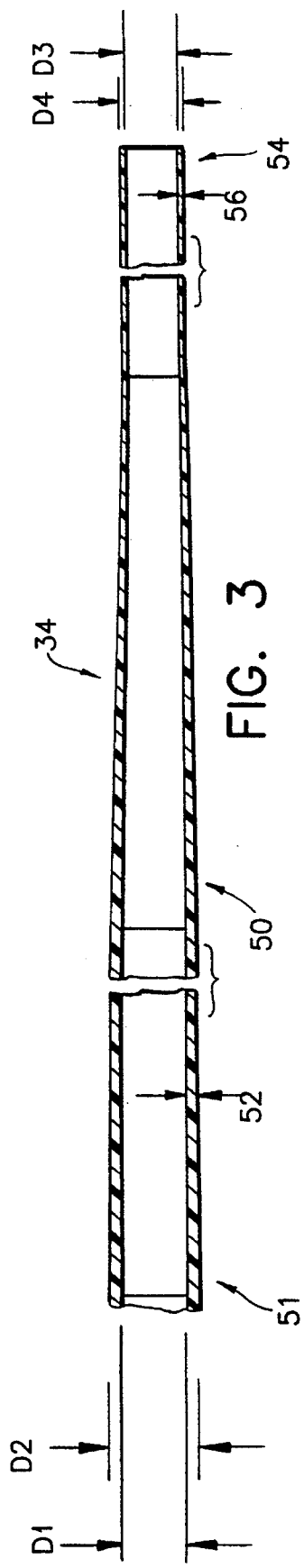
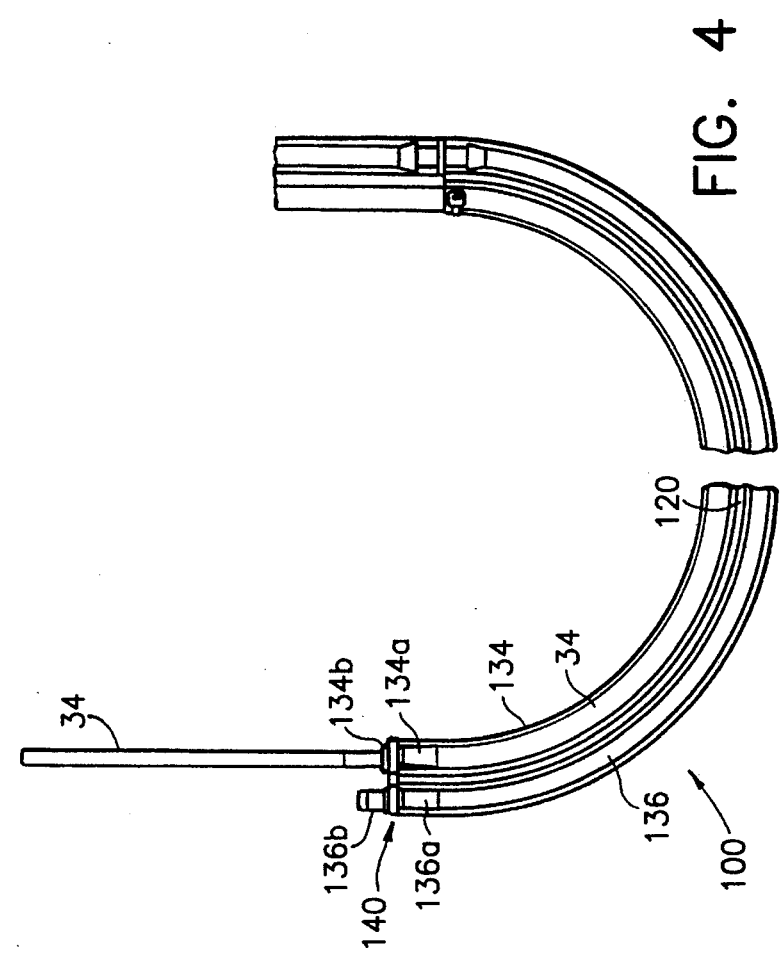
FIG. 3
FIG. 4

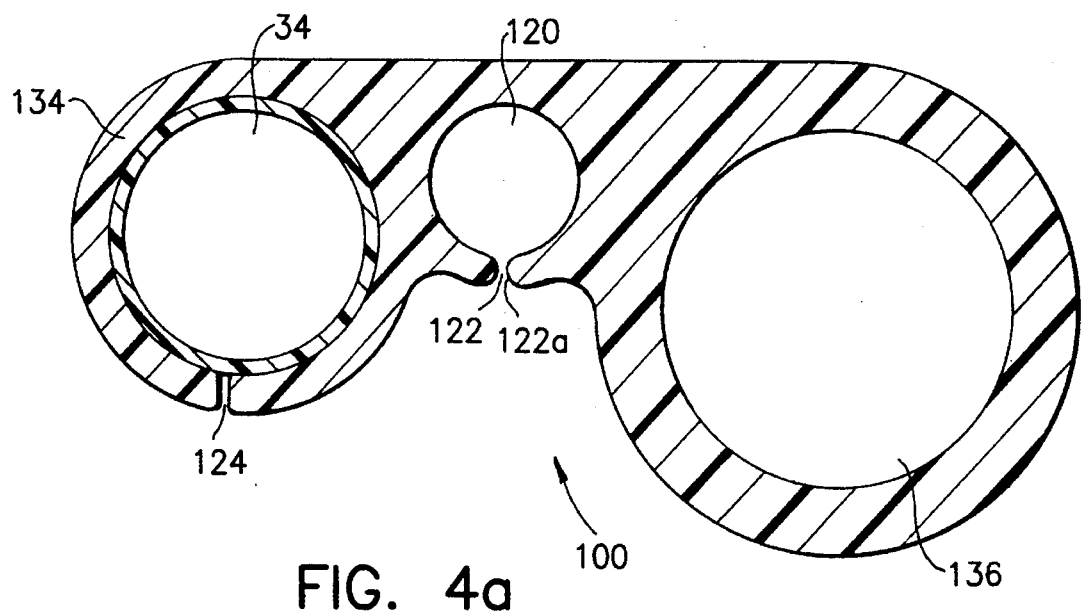
FIG. 4a
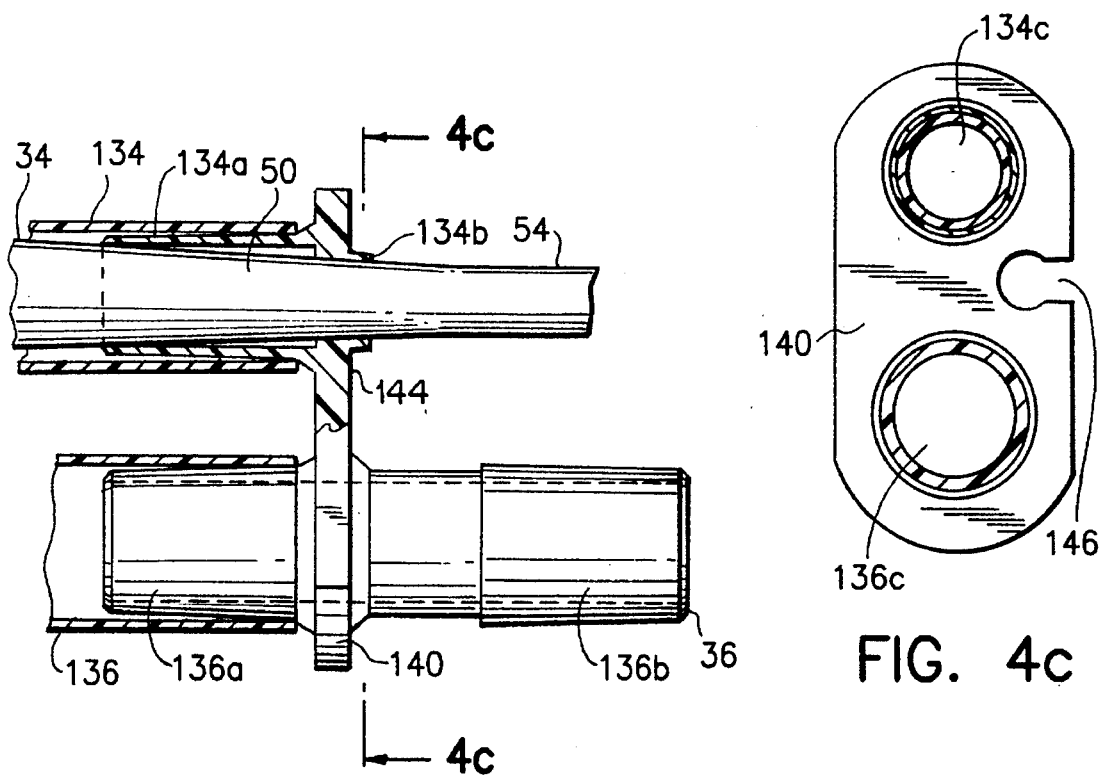
FIG. 4b
FIG. 4c

FLEXIBLE TUBE HAVING A TAPERED DIAMETER PORTION FOR USE WITH ENDOSCOPIC IRRIGATION INSTRUMENTS

This application is a continuation-in-part of co-assigned Ser. No. 07/959,280, filed Oct. 9, 1992, now U.S. Pat. No. 5,314,406, which is hereby incorporated herein by reference in its entirety.

BACKGROUND OF THE INVENTION

1. Field of the Invention

The present invention relates to endoscopic irrigation instruments. More particularly, the present invention relates to a tapered irrigation tube which permits an endoscopic irrigation instrument to be used with irrigation sources of different pressures.

2. State of the Art

Endoscopic suction-irrigation instruments are used for supplying suction and irrigation to a surgical site during endoscopic surgery. Irrigation fluid is introduced to the surgical site through an irrigation tube to rinse away blood and other matter. Suction applied through a suction tube removes the fluid with the waste. In the past, many incisions were made during surgery to allow insertion of separate suction and irrigation tubes as well as the endoscopic instruments used in the surgery. Recently, in order to reduce the number of incisions in the body, single instruments have been utilized incorporating both irrigation and suction.

Instruments which incorporate both suction and irrigation are typically connected by flexible tubes to separate suction and irrigation sources. Parent application, Ser. No. 07/959,280 discloses an endoscopic electrosurgical suction-irrigation instrument having a cannula fitted in a fluid chamber, with suction and irrigation tubes coupled to the chamber. Pinch valves coupled to triggers are used to control the flow of fluid through the tubes.

There are various constraints on the design of an endoscopic irrigation instrument. For example, the irrigation supply tube must be constructed to be strong enough to contain fluid located therein which may be pressurized to different pressures when the supply tube is pinched off, but also thin and flexible enough to allow a pinch valve in the instrument to pinch off the flow of fluid through the tube. At the same time it is desirable to provide a tube which enables as large a fluid flow stream as possible in the endoscopic irrigation instrument. These conflicting requirements must be balanced. The irrigation system in the parent application balances these requirements by providing an irrigation tube with a small diameter which is coupled at one end to the fluid chamber and on the other end to a connector inside the instrument, and a second tube of a larger diameter at the outside of the instrument which is coupled to the other side of the connector and to the irrigation source. The small irrigation tube at the inside of the instrument permits the pinch valve to stop the flow of the fluid through the tube when desired. The large diameter irrigation tube at the outside of the instrument allows more flow from the irrigation source to the instrument.

A disadvantage of the arrangement of the instrument disclosed in parent application is that when a high pressure fluid source is applied through the irrigation tube, the connector between the smaller and larger diameter tube can leak, and/or the tubes disconnect. A possible solution to this problem is to use a single thin tube from the irrigation source up to the fluid chamber of the endoscopic irrigation instrument. However, with the smaller diameter tube there would be less flow from the source than if the larger diameter tube were used.

SUMMARY OF THE INVENTION

It is therefore an object of this invention to provide an endoscopic irrigation instrument which utilizes a tapered diameter irrigation supply tube so that the instrument can be used with both higher and lower irrigation pressures and still provide a good flow.

It is another object of this invention to provide an endoscopic irrigation instrument with a tapered irrigation supply tube where the taper positions the tube within the instrument.

It is a further object of this invention to provide an endoscopic irrigation instrument with a tapered irrigation supply tube which reduces the number of connections required and thus reduces the possibility of leakage at high pressure.

In accord with these objects which will be discussed below, the endoscopic irrigation instrument of the invention broadly includes a fluid chamber, a cannula coupled to a distal end of the fluid chamber, a tapered irrigation tube which couples at its proximal end to a fluid source and which couples at its distal end to an irrigation port of the fluid chamber, and a pinch valve which controls the flow of fluid from the irrigation source to the fluid chamber and hence through the cannula to the surgical site. For purposes herein, in describing the irrigation tube, the "proximal end" relates to the end furthest away from the pinch valve and fluid chamber (i.e., the irrigation source end), while the "distal end" relates to the end closest to or in the instrument. The tapered irrigation tube is preferably arranged so that it has a first relatively larger constant inner diameter and relatively larger wall thickness on its proximal end until it starts to taper down in both inner diameter and wall thickness at a location slightly proximal the pinch valve. By the time the tapered irrigation tube passes the pinch valve in the endoscopic instrument, the tapered irrigation tube is at a second relatively smaller constant inner diameter and a relatively smaller wall thickness. The tapered irrigation tube thus enables a greater fluid flow, a pinch valve control at the thin distal end, and a tube reliability at both high and low fluid pressures.

A preferred aspect of the electrosurgical suction-irrigation instrument is to provide the instrument with a shell or connector having an opening sized between the smaller and larger outer diameters of the tapered tube so that the taper of the tapered tube is located in the opening.

Additional objects and advantages of the invention will become apparent to those skilled in the art upon reference to the detailed description taken in conjunction with the provided figures.

BRIEF DESCRIPTION OF THE DRAWINGS

FIG. 1 is a perspective view of a suction-irrigation instrument of the invention showing irrigation and suction source connections for the instrument;

FIG. 1a is a detail of an indicated portion of FIG. 1 showing a slit valve;

FIG. 3 is a longitudinal cross-sectional view of the tapered irrigation tube of the invention;

FIG. 4 is a longitudinal view of a molded tubing of the invention;

FIG. 4a is a cross-sectional view of tubing used in conjunction the suction-irrigation instrument of the invention, with the tapered tubing contained in one portion of another tubing;

FIG. 4b is a side view of a connector which mates with the molded tubing on the outside of the instrument and connects to the shell of the instrument; and FIG. 4c is a cross-sectional view of the connector of FIG. 4b.

DETAILED DESCRIPTION OF THE PREFERRED EMBODIMENT

Figure 2:
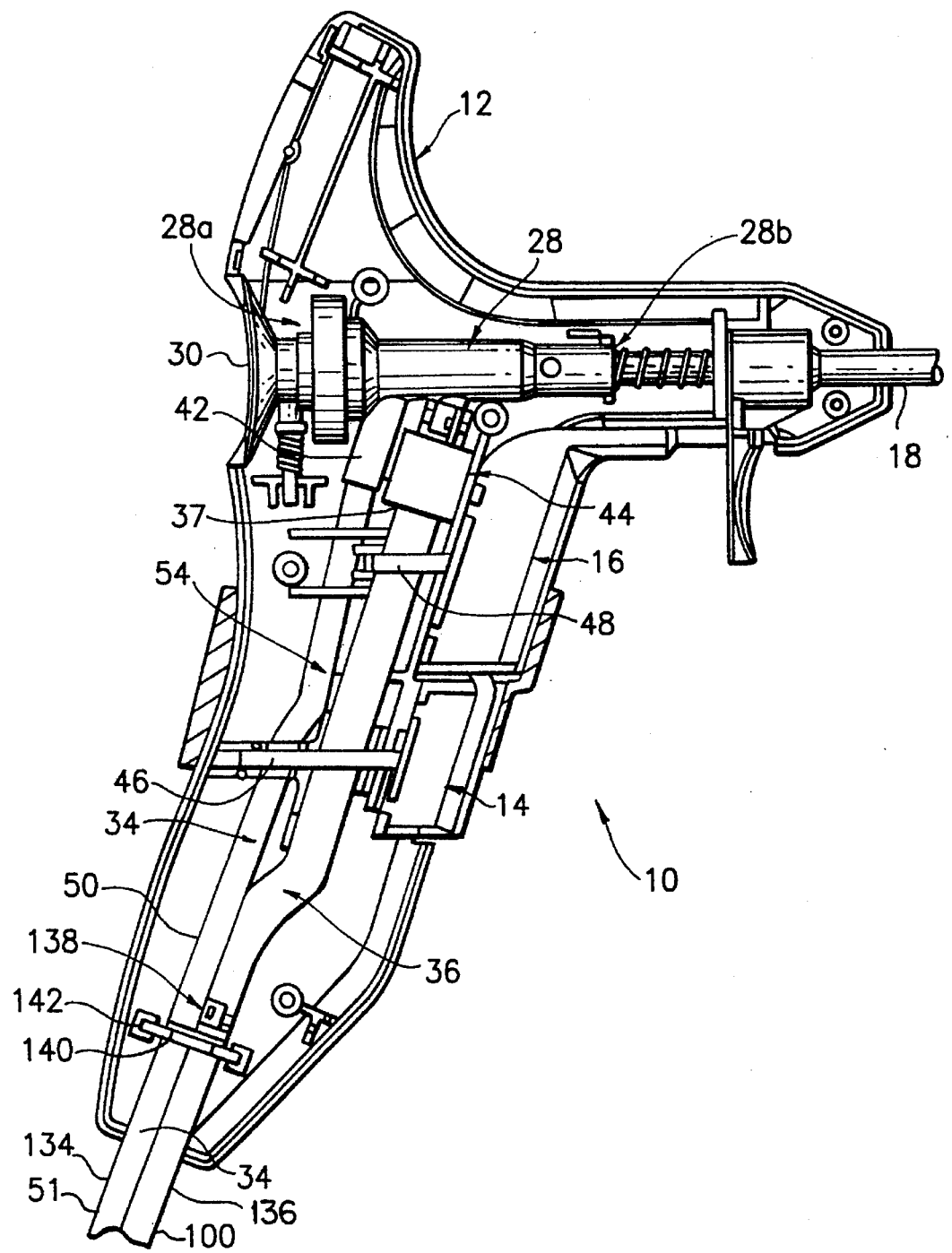
FIG. 2 is a side view of the instrument of FIG. 1 with one half of a shell removed.

Referring now to FIGS. 1, 1a and 2, an endoscopic electrosurgical suction-irrigation instrument 10 is shown having a pistol-shaped shell 12, an irrigation trigger 14, a suction trigger 16, a cannula 18, a triple lumen extruded tubing 100, a tapered irrigation supply tube 34 and a suction tube 36. The instrument 10 is connected to an irrigation fluid source 22, and a suction source 24 via the tubing 100. The irrigation fluid source 22 may be a relatively low pressure source (e.g., 40 psi) or a relatively high pressure source (e.g., 100 psi) depending on availability and/or application required.

Within the shell 12 is located a fluid chamber 28 with a proximal end 28a and a distal end 28b (see FIG. 2). The cannula 18 is coupled to the distal end 28b of the fluid chamber 28 and extends distally therefrom. As shown in FIGS. 1a and 2, a slit-valve 30 and sealing gasket 32 are provided at the proximal end 28a of the fluid chamber 28 to prevent the loss of fluid through the proximal end 28a of the fluid chamber. The slit-valve 30 prevents leakage from the instrument 10 when no tool is inserted through the proximal end 28a of the fluid chamber 28, and the sealing gasket 32 prevents leakage when a probe such as probe 26 shown in FIG. 1 is inserted through the proximal end 28a of the fluid chamber 28 and into and through the cannula 18.

The fluid chamber 28 of the endoscopic irrigation instrument 10 is provided with an irrigation port 42 and a suction port 44 to which are respectively coupled an irrigation tube 34 and a suction tube 36. The irrigation port 42 is preferably located proximal to the suction port 44 as discussed more fully in the parent application hereto Ser. No. 07/959,280, now U.S. Pat. No. 5,314,406. The distal end of the irrigation tube 34 is preferably bonded to the irrigation port 42 and the suction tube 36 is preferably coupled to the suction port 44 by an elastic limit protector 37.

The irrigation and the suction triggers 14 and 16 open and close an irrigation pinch valve 46 and a suction pinch valve 48. The irrigation pinch valve 46 controls the flow of fluid from the irrigation source 22, through the irrigation tube 34, through the fluid chamber 28 and through the cannula 18 to the surgical site, while the suction pinch valve 48 controls the application of a vacuum from the suction source 24, through the suction tube 36, through the fluid chamber 28 and through the cannula 18 to the surgical site. The general functions of the triggers 14 and 16, the valves 46 and 48, and the fluid chamber 28 are described more fully in the parent application Ser. No. 07/959,280, now U.S. Pat. No. 5,314,406.

Referring now to FIG. 3, the irrigation supply tube 34 of the invention is shown with a tapered portion 50 which tapers from a proximal end 51 of a relatively constant diameter to a distal end 54 of relatively constant inner diameter. The proximal end 51 has an inner diameter D1, an outer diameter D2 and a first thickness 52, while the distal end 54 has an inner diameter D3, an outer diameter D4 and a second thickness 56. For the particular suction-irrigation apparatus disclosed in parent Ser. No. 07/959,280, the preferable dimensions of the proximal end 51 and the distal end 54 are as follows:

| proximal end | | distal end | |
| --- | --- | --- | --- |
| inner diameter D1: | 0.185 in. | inner diameter D3: | 0.130 in. |
| outer diameter D2: | 0.269 in. | outer diameter D4: | 0.178 in. |
| thickness 52: | 0.042 in. | thickness 54: | 0.024 in. |

The length of the irrigation tube 34 from the proximal end 51 to the distal end 54 is preferably 51.250 inches at a minimum, while the length of the tapered portion 50 of the irrigation tube 34 can vary as desired, but is preferably about 4.00 inches in length.

The preferred method of manufacture of the irrigation tube 34 is to extrude medical grade PVC. By increasing the speed of the extrusion press during extrusion, the tube 34 can be made to taper from a larger diameter to a smaller diameter, with the wall thickness also tapering. It should be appreciated, however, that it is possible to obtain such a tapered irrigation tube through the use of molding or other techniques.

The tapered irrigation tube 34 solves the problems inherent with the tube configurations of the prior art. In particular, since most of the tube has a larger diameter, the flow through the tube is much larger than the flow through a tube of smaller diameter. At the same time, because the tube has a tapered portion 50, a tube of smaller diameter and thickness is presented to the pinch valve 46 which can effectively control fluid flow without leakage problems. In addition, any high pressure seen by the smaller diameter section of the tube is for a short period of time, thereby minimizing creep failure. Further, because a single tube is tapering from the relatively larger diameter and relatively larger wall thickness to the relatively smaller diameter and relatively smaller wall thickness, a fluid coupling which was used to couple a larger tube to a smaller tube is eliminated. Therefore, at high fluid pressures, the possibility of leaking at this coupling is eliminated.

Returning to FIG. 2, it is seen that the thin distal end 54 of the irrigation tube 34 couples to the irrigation port 42 of the fluid chamber 28. The thin distal end 54 extends proximally past the irrigation pinch valve 46 before it tapers at its tapered portion 50. As is described in more detail hereinafter, the taper 50 of the irrigation tube 34 fittingly engages an opening in a connector 142 located in the shell 12, thereby securing and locating the irrigation tube 34 in the shell 12.

The shell 12 receives the irrigation supply tube 34 via a preferred triple lumen tubing 100 described in detail in the parent application Ser. No. 07/959,280, now U.S. Pat. No. 5,314,406. The triple lumen tubing 100 incorporates an irrigation conduit 134, a suction-vacuum conduit 136, and a groove 120 therebetween as shown in FIGS. 4 and 4a. The irrigation conduit 134 is mostly closed but is provided with a slit 124 so that the irrigation tube 34 can be fitted inside. Because the tubing 100 is elastic, the irrigation tube 34 can be inserted inside the irrigation conduit 134 and remain secure within. The suction conduit 136 is similar to the irrigation conduit 134 but has a larger diameter, has no slit and acts as a continuation of the suction tube 36. The groove 120 is mostly closed but is also provided with a slit 122 defined by a pair of lips 122a extending along the length of the tubing 100 to allow insertion of an electrical supply wire into the groove 120. Other embodiments of the tubing and a detailed description of the groove 120 are discussed more fully in the parent application hereto.

The tubing 100 is coupled to the shell 12 of the instrument 10 by a connector 140 which fits in a connecting groove 142 in the shell 12 (see FIG. 2). The connector 140, as shown in FIGS. 4, 4b and 4c, includes a central block 144 having tapered couplings 134a, 136a, 136b, and a tapered shoulder 134b. The tapered couplings 134a and 136a are provided to respectively couple to the irrigation tube holder 134 (not the tube 34) and suction conduit 136 of the tubing 100. In particular, the tapered couplings 134a and 136a fittingly engage the inside of the irrigation and suction conduits 134 and 136 of the tubing 100. On the other side of the connector 140, the tapered coupling 136b is provided to couple to the suction tube 36 located on the inside of the shell 12. Typically, the suction tube 36 is bonded to the tapered coupling 136b and secured by a tie strap 138. Preferably, the diameter of the inner suction coupling 136b is smaller than the diameter of the outer suction coupling 136a. In this manner, a connection to a smaller suction tube 36 on the inside of the shell 12 is provided, which permits pinching off by the pinch valve 48. What is of most importance, however, is that since only one irrigation tube 34 is used for the instrument, a coupling for a second inner irrigation tube is not required. Indeed, it is exactly this coupling which is effectively eliminated by use of the tapered irrigation tubing. Thus, in lieu of a inner irrigation tube coupling, a shoulder 134b is provided. The shoulder 134b provides a stop location to the tapered portion 50 of the irrigation tube 34. In particular, somewhere along the tapered portion 50 of the irrigation tube 34, the tapered portion 50 fittingly engages within the shoulder 134b of the connector 140, thereby preventing the irrigation tube 34 from sliding further into the shell 12.

FIG. 4c shows the connector 140 in cross section along line 4c—4c of FIG. 4b. It can be seen that the connector 140 has irrigation and suction throughbores 134c and 136c and that the central block 144 is provided with a wire space 146 having an opening corresponding to the groove 120 on the tubing 100. The distal end 54 of the irrigation tube 34 extends through the irrigation throughbore 134c to the irrigation port 42 while suction can be applied through the suction throughbore 136c from the suction source 24. The wire space 146 on the central block 144 provides a place to secure the electrical supply wire that attaches to the inside of the instrument as described more fully in the parent application Ser. No. 07/959,280, now U.S. Pat. No. 5,314,406. The central block 144 is flange-like to allow it to be easily coupled to the connecting groove 142 in the shell 12.

There have been described and illustrated herein an endoscopic irrigation surgical instrument. While particular embodiments of the invention have been described, it is not intended that the invention be limited thereto, as it is intended that the invention be as broad in scope as the art will allow and that the specifications be read likewise. Thus, while particular dimensions have been described as preferred, the lengths, diameters, etc., of the portions of the tapered irrigation tube can be changed. For example, and as an extreme, the irrigation tube need not be provided with a portion which is of constant smaller diameter. In other words, at the connection between the irrigation tube and the fluid chamber, the tube can still be tapering. While this is not a preferred embodiment, it will be appreciated that it will not significantly reduce the functionality of the instrument when the irrigation trigger is located almost directly adjacent the fluid chamber. Likewise, rather than having a thin distal end of relatively small diameter which either tapers down or continues at a constant diameter, the irrigation tube may be molded or otherwise formed to assume an hour-glass configuration. In other words, the irrigation tube would be arranged to be of smaller inner diameter and thickness only at the location of the pinch valve. Also, while the tapered irrigation tube was described as being located in a conduit of another tube which also has a suction conduit, it will be appreciated that such an arrangement is not necessary. In particular, if separate suction and irrigation tubes were utilized away from the shell of the instrument, the tapered irrigation tube would not have to be inserted into another tube which is only acting as a holder for the irrigation tube. In addition, while the tapered irrigation tube was shown as being located in the smaller irrigation lumen of a multi-lumen tube, (i.e., a tube with a plurality of conduits) it should be appreciated that the larger lumen of such a multi-lumen tube could be used for irrigation. In such a situation, the tapered irrigation tube would be placed in the larger lumen, with the smaller lumen of the multi-lumen tube being used for suction. Further, while the tubing of the invention was described as being extruded, it will be appreciated that other manufacturing techniques such as molding could be utilized. It will therefore be appreciated by those skilled in the art that yet other modifications could be made to the provided invention without deviating from its spirit and scope so claimed.

We claim:

1. An endoscopic irrigation instrument for use with a pressurized source of irrigation fluid, comprising:

a) a flexible irrigation tube having a proximal end having a first inner diameter, a distal portion having a second inner diameter smaller than said first inner diameter, and a portion of tapered inner diameter which tapers from said first inner diameter to said second inner diameter, with said proximal end being coupled to the irrigation source;

b) a pinch valve means located adjacent said distal portion of said flexible irrigation tube, said pinch valve means for pinching said flexible irrigation tube and controlling flow of the irrigation fluid through said irrigation tube at a location of said flexible irrigation tube other than where said flexible irrigation tube has said first inner diameter;

c) a fluid chamber which receives said distal portion of said flexible irrigation tube; and d) a cannula having a proximal end coupled to said fluid chamber.

2. An endoscopic irrigation instrument according to claim 1, wherein:

said proximal end of said irrigation tube has a first wall thickness and said distal portion of said irrigation tube has a second wall thickness, wherein said second wall thickness is smaller than said first wall thickness.

3. An endoscopic irrigation instrument according to claim 2, wherein:

said distal portion of said irrigation tube includes a portion of constant inner diameter, said constant inner diameter being said second inner diameter, and said pinch valve means pinches said irrigation tube at a location of said irrigation tube where said irrigation tube has said second inner diameter.

4. An endoscopic irrigation instrument according to claim 3, further comprising:

e) a shell including substantially circular opening means of a third diameter for receiving said irrigation tube, wherein said proximal portion of said irrigation tube has a first outer diameter and said distal end of said irrigation tube has a second outer diameter smaller than said first outer diameter, and said third diameter is smaller than said first outer diameter and greater than said second outer diameter.

5. An endoscopic irrigation instrument according to claim 4, wherein:

said third diameter is chosen and said irrigation tube is arranged such that a first distance between said opening and said fluid chamber is substantially equal to a second distance between a distal end of said irrigation tube and a location on said irrigation tube where said irrigation tube has an outer diameter equal to said third diameter.

6. An endoscopic irrigation instrument according to claim 4, further comprising:

an integral plastic tubing having a separate irrigation conduit and a separate suction conduit,
wherein said irrigation tube extends through said irrigation conduit of said plastic tubing.

7. An endoscopic irrigation instrument according to claim 6, wherein:

said circular opening means includes a connector means for receiving said integral molded tubing, with said separate suction conduit and said separate irrigation conduit both terminating at said connector means, and said integral plastic tubing extending through said circular opening means, and said endoscopic irrigation instrument further includes a suction tube coupled to said connector means and to said fluid chamber, and a second pinch valve means for pinching off said suction tube.

8. An endoscopic irrigation instrument according to claim 1, further comprising:

an integral plastic tubing having a separate irrigation conduit and a separate suction conduit,
wherein said irrigation tube extends through said irrigation conduit of said plastic tubing.

9. An endoscopic irrigation instrument according to claim 1, further comprising:

e) a shell including substantially circular opening means of a third diameter for receiving said irrigation tube, wherein
said proximal portion of said irrigation tube has a first outer diameter and said distal end of said irrigation tube has a second outer diameter smaller than said first outer diameter, and said third diameter is greater than said second outer diameter and smaller than said first outer diameter.

10. An endoscopic irrigation instrument according to claim 9, wherein:

said third diameter is chosen and said irrigation tube is arranged such that a first distance between said opening and said fluid chamber is substantially equal to a second distance between the distal portion of said irrigation tube and a location on said irrigation tube where said irrigation tube has an outer diameter equal to said third diameter.

11. An endoscopic irrigation instrument according to claim 9, further comprising:

an integral plastic tubing having a separate irrigation conduit and a separate suction conduit,
wherein said irrigation tube extends through said irrigation conduit of said plastic tubing.

12. An endoscopic irrigation instrument according to claim 11, wherein:

said circular opening means includes a connector means for receiving said integral plastic tubing, with said separate suction conduit and said separate irrigation conduit both terminating at said connector means, and said integral plastic tubing extending through said circular opening means, and said endoscopic irrigation instrument further includes a suction tube coupled to said connector means and to said fluid chamber, and a second pinch valve means for pinching off said suction tube.

\* \* \* \* \*